(12) United States Patent
Ionkin

(10) Patent No.: US 6,566,297 B2
(45) Date of Patent: May 20, 2003

(54) AMINONITRILE PRODUCTION

(75) Inventor: Alex Sergey Ionkin, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/801,029

(22) Filed: Mar. 7, 2001

(65) Prior Publication Data

US 2001/0047104 A1 Nov. 29, 2001

Related U.S. Application Data

(60) Provisional application No. 60/188,661, filed on Mar. 10, 2000.

(51) Int. Cl.[7] .................. B01J 31/00; B01J 27/188; B01J 27/185; B01J 23/00; B01J 23/32
(52) U.S. Cl. .................. 502/164; 502/166; 502/210; 502/213; 502/313; 502/314; 502/315; 502/316; 502/324; 502/326
(58) Field of Search ................. 502/210, 213, 502/313–316, 164, 166, 324, 326

(56) References Cited

U.S. PATENT DOCUMENTS

| | | | |
|---|---|---|---|
| 2,208,598 A | 7/1940 | Rigby | |
| 2,257,814 A | 10/1941 | Rigby | |
| 2,762,835 A | 9/1956 | Swerdloff | |
| 3,322,815 A | 5/1967 | Feldman et al. | |
| 3,350,439 A | 10/1967 | Feldman et al. | |
| 3,591,618 A | 7/1971 | Hanschke et al. | |
| 4,389,348 A | 6/1983 | Diamond et al. | |
| 4,601,859 A | 7/1986 | Galle et al. | |
| 5,151,543 A | 9/1992 | Ziemecki | |
| 5,296,628 A | 3/1994 | Sanchez | |
| 5,512,697 A | 4/1996 | Schnurr et al. | |
| 5,527,946 A | 6/1996 | Flick et al. | |
| 5,986,127 A | 11/1999 | Ionkin et al. | |
| 6,011,179 A | * 1/2000 | Haas et al. | 564/448 |
| 6,080,884 A | 6/2000 | Ziemecki et al. | |
| 6,087,296 A | * 7/2000 | Harper | 502/301 |
| 6,156,694 A | * 12/2000 | Harper | 502/301 |
| 6,258,745 B1 | * 7/2001 | Ionkin et al. | 502/326 |

FOREIGN PATENT DOCUMENTS

| | | |
|---|---|---|
| DE | 836 938 | 7/1949 |
| DE | 848 654 | 7/1949 |
| DE | 19636 768 A1 | 12/1998 |
| WO | WO 99/47492 | 9/1999 |

* cited by examiner

Primary Examiner—Mark L. Bell
Assistant Examiner—Patricia Hailey
(74) Attorney, Agent, or Firm—Bart E. Lerman

(57) ABSTRACT

Provided is a selective hydrogenation process for producing aminonitriles by contacting the corresponding dinitriles with a hydrogen-containing fluid in the presence of a hydrogenation catalyst, a solvent and tetraalkylammonium hydroxide and/or tetraalkylphosphonium hydroxide additive.

20 Claims, No Drawings

AMINONITRILE PRODUCTION

CROSS-REFERENCE TO RELATED APPLICATION

This application claims priority under 35 U.S.C. §119 from U.S. Provisional Application Ser. No. 60/188,661 (filed Mar. 10, 2000), which is incorporated by reference herein as if fully set forth.

FIELD OF THE INVENTION

The invention relates to a selective hydrogenation process for producing aminonitriles in the presence of a tetraalkylammonium and/or tetraalkylphosphonium hydroxide additive.

BACKGROUND OF THE INVENTION

Aminonitriles are a class of important chemicals that have a variety of industrial applications. For example, aminonitriles can be used as monomers for producing high molecular weight polyamides. Specifically, 6-aminocapronitrile can be used to produce nylon 6.

Aminonitriles can be produced by catalytic partial hydrogenation of dinitriles. See, for example, U.S. Pat. Nos. 2,208,598, 2,257,814, 2,762,835, 3,322,815, 3,350,439, 3,591,618, 4,389,348, 4,601,859, 5,151,543, 5,296,628, 5,512,697, 5,527,946, DE836938, DE848654, DE-A-19636768 and WO99/47492 (corresponding to U.S. Pat. No. 5,986,127 and U.S. 6,080,884), all of which are incorporated by reference herein for all purposes as if fully set forth. However, the yield of and selectivity to a desired aminonitrile using some of the known processes may not be as high as desired, and the amount of the complete hydrogenation product (diamine) is also generally higher than desired.

U.S. Pat. No. 5,986,127 mentioned above describes the use of certain carbonyl group-containing compounds as additives in the partial hydrogenation process to improve the yield of and/or selectivity to the desired aminonitrile product, and/or reduce the amount of fully hydrogenated product (diamine) produced.

We have now found new classes of compounds that also effectively function as improved yield and/or selectivity additives in the partial hydrogenation processes such as, for example, those mentioned in previously incorporated U.S. Pat. No. 5,986,127.

SUMMARY OF THE INVENTION

In accordance with one aspect of the present invention, there is provided a process for the partial hydrogenation of a dinitrile to an aminonitrile, comprising the step of contacting the dinitrile with a hydrogen-containing fluid in the presence of (a) a solvent comprising liquid ammonia, an alcohol, or both; (b) a hydrogenation catalyst; and (c) an additive comprising a compound selected from the group consisting of a tetraalkylammonium hydroxide compound and a tetraalkylphosphonium hydroxide compound.

In accordance with another aspect of the present invention, there is provided an improved process for preparing an aminonitrile from a corresponding dinitrile by contacting the dinitrile with a hydrogen-containing fluid in the presence of a solvent and a hydrogenation catalyst, wherein the improvement comprises contacting the dinitrile, hydrogen-containing fluid, solvent and hydrogenation catalyst in the further presence of an additive comprising a compound selected from the group consisting of a tetraalkylammonium hydroxide compound and a tetraalkylphosphonium hydroxide compound.

Another aspect of the present invention relates to a method for improving the yield of and/or selectivity to an aminonitrile obtained by partially hydrogenating a corresponding dinitrile with a hydrogen-containing fluid in the presence of a solvent and a hydrogenation catalyst, comprising the step of partially hydrogenating the dinitrile in the further presence of an effective amount of an additive comprising a compound selected from the group consisting of a tetraalkylammonium hydroxide compound and a tetraalkylphosphonium hydroxide compound.

In yet another aspect of the present invention, there is provided a catalyst composition comprising a combination of (1) a hydrogenation catalyst suitable for hydrogenating a dinitrile to an aminonitrile; and (2) an additive comprising a compound selected from the group consisting of a tetraalkylammonium hydroxide compound and a tetraalkylphosphonium hydroxide compound.

An advantage of this invention is that an aminonitrile can be produced in higher yield and/or having a higher selectivity to the aminonitrile with the additive than without. Other objects and advantages will become more apparent as the invention is more fully disclosed herein below.

DETAILED DESCRIPTION OF THE PREFERRED EMBODIMENTS

According to this invention, a dinitrile is contacted with a hydrogen-containing fluid in the presence of a solvent, a catalyst and a tetraalkylammonium hydroxide compound and/or a tetraalkylphosphonium hydroxide compound.

Suitable dinitriles for use herein have the general formula $R(CN)_2$, wherein R is a hydrocarbylene group selected from the group consisting of an alkylene, arylene, alkenylene, alkarylene and aralkylene group. One dinitrile or combinations of different dinitriles may be used. Preferred hydrocarbylene groups contain from 2 to 25, more preferably 2 to 15, and most preferably 2 to 10 carbon atoms per group. In other words, preferred dinitriles contain from 4 to 27, more preferably 4 to about 17, and most preferably 4 to 12, carbon atoms per dinitrile molecule. The preferred type of hydrocarbylene group is an alkylene group.

Examples of suitable dinitriles include, but are not limited to, adiponitrile; methylglutaronitrile; alpha,omega-pentanedinitrile; alpha,omega-heptanedinitrile; alpha,omega-nonanedinitrile; alpha,omega-dodecanedinitrile; alpha,omega-pentadecanedinitrile; alpha,omega-icosanedinitrile; alpha,omega-tetracosane-dinitrile; 3-methylhexanedinitrile; 2-methyl-4-methylene-octanedinitrile; and combinations of two or more thereof.

Preferably the carbon atoms of the starting dinitrile are arranged in a branched or linear chain. Preferred examples are adiponitrile (hydrogenated to 6-aminocapronitrile), methylglutaronitrile (hydrogenated to two isomeric aminonitriles: 5-amino-2-methylvaleronitrile and 5-amino-4-methylvaleronitrile) and alpha,omega-dodecanedinitrile (hydrogenated to the corresponding aminonitrile). The preferred dinitrile is adiponitrile because its selective hydrogenation product, 6-aminocapronitrile, is a well-known monomer for polymerization applications.

Any hydrogen-containing fluid can be used in the invention as long as there is sufficient hydrogen in the fluid to selectively hydrogenate a dinitrile to an aminonitrile. The term "fluid" refers to liquid, gas or both. The hydrogen content in the fluid can range from 1 to 100%, preferably about 50 to about 100%, and most preferably 90 to 100% by volume. The presently preferred hydrogen-containing fluid is substantially pure hydrogen gas.

The molar ratio of hydrogen (in the hydrogen-containing fluid) to dinitrile is not critical as long as sufficient hydrogen is present to produce the desired aminonitrile. Hydrogen is generally used in excess. Hydrogen pressures are generally in the range of about 50 to about 2000 psig (about 0.45 to about 13.89 MPa), with from about 200 to about 1000 psig (about 1.48 to about 7.00 MPa) preferred.

Any solvent that comprises either liquid ammonia or an alcohol can be used in the invention. The concentration of liquid ammonia in the solvent can range from about 20 to about 100%, preferably about 50 to about 100%, and most preferably about 80% to about 100%, by weight of total solvent. A substantially pure liquid ammonia is preferred. However, if an alcohol is also present in the solvent, the concentration of ammonia can be adjusted based on the quantity of alcohol used, which is discussed in further detail below. The molar ratio of ammonia to dinitrile is preferably about 1:1 or greater, and is generally in the range of from about 1:1 to about 30:1, more preferably from about 2:1 to about 20:1.

Any alcohol that can facilitate the selected hydrogenation of a dinitrile to an aminonitrile can be used in this invention. Preferred are alcohols with 1 to 10, more preferably 1 to 4, carbon atoms per molecule. Examples of suitable alcohols include, but are not limited to, methanol, ethanol, propanol, isopropyl alcohol, butanol, isobutyl alcohol, pentanol, hexanol, heptanol, octanol, nonanol, decanol, and combinations of two or more thereof. The most preferred alcohol (when used) is methanol. The alcohol can generally be present in the solvent in the concentration of from about 20 to about 100%, preferably about 30 to about 99%, by weight based on the total solvent weight.

Typically when an alcohol is use, the solvent further comprises a base that is substantially soluble in the solvent. The term "substantially" refers to "more than trivial". Preferred bases are ammonia, an ammonium base or an inorganic base such as, for example, alkali metal oxides, alkaline earth metal oxides, alkali metal hydroxides, alkaline earth metal hydroxides, partially neutralized acids in which one or more protons of the acids are replaced with ammonium ion, alkali metal ions, alkaline earth metal ions, or combinations of two or more thereof. Specific examples of suitable bases include, but are not limited to ammonia, lithium hydroxide, sodium hydroxide, potassium hydroxide, sodium bicarbonate, sodium carbonate, potassium bicarbonate, or combinations of two or more thereof. The most preferred bases are ammonia, lithium hydroxide and sodium hydroxide for they are readily available and inexpensive.

A base can be present in the solvent in any quantity so long as the quantity can facilitate the selective hydrogenation of a dinitrile to an aminonitrile. Generally, a base can be present in the solvent in the range of from about 0.1 to about 10 weight %, based on the total weight of the starting dinitrile.

The catalyst in the process is a hydrogenation catalyst suitable for hydrogenating a dinitrile to an aminonitrile. Preferred are catalysts based on transition metals selected from the group consisting of iron, cobalt, nickel, rhodium and combinations thereof. The catalyst may also contain one or more promoters in addition to the transition metals mentioned above, for example, one or more of Group VIB and Group VII metals such as chromium, molybdenum and tungsten. The catalyst can also be in the form of an alloy, including a solid solution of two or more metals, or an individual metal.

The catalytic metal can also be supported on an inorganic support such as alumina, magnesium oxide and combinations thereof. The metal can be supported on an inorganic support by any means known to one skilled in the art such as, for example, impregnation, coprecipitation, ion exchange, and combinations of two or more thereof. The preferred inorganic support is magnesium oxide, and the preferred supported catalyst is a magnesium oxide supported nickel-iron catalyst.

The catalyst can be present in any appropriate physical shape or form. It can be in fluidizable forms, extrudates, tablets, spheres or combinations of two or more thereof. The catalyst may be in sponge metal form, for example, the Raney® nickels and Raney® cobalts. The molar ratio of catalyst to dinitrile can be any ratio as long as the ratio can catalyze the selective hydrogenation of a dinitrile. The weight ratio of catalyst to dinitrile is generally in the range of from about 0.0001:1 to about 1:1, preferably about 0.001:1 to about 0.5:1. If the catalytic metal is supported on an inorganic support or is a portion of alloy or solid solution, the catalytic metal is generally present in the range of from about 0.1 to about 60, preferably about 1 to about 50, and most preferably about 2 to about 50 weight %, based on the total catalyst weight.

The preferred catalyst is a sponge metal type catalyst. The metallic component is iron, cobalt, nickel or combinations thereof. Commercially available catalysts of this type are promoted or unpromoted Raney® Ni or Raney® Co catalysts that can be obtained from the Grace Chemical Co. (Columbia, Md.), or alternative sponge metal catalysts available, for example, from Activated Metals Corporation (Sevierville, Tenn.) or Degussa (Ridgefield Park, N.J.).

In the case of the preferred supported nickel/iron catalyst, the rate of adiponitrile conversion increases with the amount of Ni deposited on the support. The preferred concentration of Ni is between about 5 and about 50 weight %, and especially between about 25 and about 35 weight %, based on the catalyst weight (metals +support). The preferred concentration of Fe is between about 0.2 and about 20 weight %, and especially between about 0.5 and about 10 weight %, based on the catalyst weight (metals+support).

Further details on the above components can be found from various of the previously incorporated references. Specific reference may be had, for example, to U.S. Pat. Nos. 2,208,598, 2,257,814, 2,762,835, 3,322,815, 5,151, 543, 5,296,628, 5,512,697, 5,527,946 and WO99/47492 (U.S. Pat. No. 5,986,127 and U.S. 6,080,884).

A wide variety of tetraalkylammonium hydroxide and tetraalkylphosphonium hydroxide compounds have been found that can effect the selectivity/yield improvement in the invention.

The term "improvement" is referred to as enhanced selectivity to aminonitrile product at conversions greater than about 70%, preferably conversions greater than about 80%, and especially conversions greater than about 90%, as compared to the selectivity without the use of the additive of this invention. An "effective amount" of the additive is amount required to achieve the aforementioned enhanced selectivity and/or an improved overall yield of aminonitrile, as compared to without the use of the additive.

In preferred embodiments, the alkyl groups of the tetraalkylammonium and tetraalkylphosphonium hydroxide compounds each individually contain from 1 to 8 carbon atoms, and more preferably 1–4 carbon atoms. It is preferred that all four of the alkyl groups in a molecule are the same, but mixtures having different tetraalkyl substituents are suitable for use herein.

Examples of suitable tetraalkylammonium hydroxide and tetraalkylphosphonium hydroxide compounds include, but are not limited to, tetramethylammonium hydroxide, tetraethylammonium hydroxide, tetrapropylammonium hydroxide, tetrabutylammonium hydroxide and tetrabutylphosphonium hydroxide. As indicated above, combinations of two or more tetraalkylammonium hydroxide and/or tetraalkylphosphonium hydroxide compounds are also suitable.

It should be noted that various hydrated forms such as, for example, tetramethylammonium hydroxide pentahydrate, are included within the meaning of tetraalkylammonium hydroxide and tetraalkylphosphonium hydroxide.

The additive is present during the contacting in any quantity that can improve the selective hydrogenation of a dinitrile to its corresponding aminonitrile (e.g., an effective amount). Generally, the weight ratio of the additive to the catalyst is in the range of from about 0.001:1 to about 2:1, preferably about 0.005:1 to about 1:1, and especially about 0.01:1 to about 0.5:1. If the additive is used in hydrated form, this weight ratio is based on the non-hydrated tetraalkylammonium and/or tetraalkylphosphonium hydroxide compound form.

The catalyst and additive can be separately introduced into contact with a dinitrile; however, it is preferred that the catalyst, whether it is in its metal form or in an alloy or solid solution or on an inorganic support, is precontacted with the additive. This may be done in a solvent such as, for example, an alcohol, ether, ester, ammonia or combinations of two or more thereof. Further preferably the precontacting is also carried out in a hydrogen-containing fluid such as described above. Contacting of the catalyst and additive produces a pretreated catalyst. The pretreated catalyst can be washed with a solvent disclosed above, preferably under anaerobic condition to produce an additive-treated catalyst.

The contacting of the catalyst and additive can be carried out under any conditions effective to produce an additive-treated catalyst that can improve selective hydrogenation of a dinitrile or the selectivity to an aminonitrile. Generally, the entire process for producing the additive-treated catalyst can be carried out by contacting a catalyst with an additive disclosed above at a temperature in the range of from about 20° C. to about 150° C., preferably about 30° C. to about 100° C., under the same general pressures as described above, for about 5 seconds to about 25 hours. The weight ratio of additive to catalyst in the pre-contacting procedure generally ranges from about 0.01:1 to about 5:1, preferably from about 0.05:1 to about 3:1, more preferably from about 0.1:1 to about 2:1, and especially from about 0.25:1 to about 1:1.

The partial hydrogenation process of the present invention can be carried out at a temperature in the range of from about 25 to about 150° C., preferably about 40 to about 100° C., most preferably about 60 to about 80° C., at a total pressure generally in the range of about 50 to about 2000 psig (about 0.45 to about 13.89 MPa), with from about 200 to about 1000 psig (about 1.48 to about 7.00 MPa) preferred, for a time period generally in the range of from about 15 minutes to about 25 hours, preferably about 1 hour to about 10 hours.

The process of the invention can be operated batch wise or continuously in an appropriate reactor. Stirring or agitation of the reaction mixture can be accomplished in a variety of ways known to those skilled in the art. The partial hydrogenation of the starting dinitrile to its corresponding aminonitrile with high selectivity at high conversions of the dinitrile makes this process efficient and useful.

Further general and specific process details can be found from various of the previously incorporated references. Specific reference may be had, for example, to U.S. Pat. Nos. 2,208,598, 2,257,814, 2,762,835, 3,322,815, 5,151,543, 5,296,628, 5,512,697, 5,527,946 and WO99/47492 (U.S. Pat. No. 5,986,127 and U.S. 6,080,884).

The following examples further illustrate the process of the invention and are not to be construed to unduly limit the scope of the invention.

The meaning of terms used in the Examples is defined as follows:

Yield of aminonitrile is the measured concentration of aminonitrile divided by the starting concentration of dinitrile.

Conversion of the dinitrile is the difference between the starting and the instant concentration of dinitrile, divided by the starting concentration of dinitrile.

Selectivity to aminonitrile is the measured yield of aminonitrile divided by conversion of the dinitrile at that instance.

COMPARATIVE EXAMPLE 1

A sponge Ni catalyst (1.2 g) promoted with Fe and Cr (Activated Metals, A4000, without any further additives) was added to a 50 cc autoclave together with 3.2 g adiponitrile (ADN) and 35 cc of liquid ammonia to form a mixture. Hydrogen was introduced to the autoclave and the ADN was hydrogenated at 60° C. under the total pressure of 1045 psig (7.31 MPa) at ca. 1500 rpm. Total conversion of ADN was reached within 30 minutes on stream. The maximum yield of aminocapronitrile was 57% at 90% ADN conversion for a selectivitiy of 63%.

COMPARATIVE EXAMPLE 2

To a 300 cc autoclave, was charged 7.7 g Raney® Co (obtained from W.R. Grace Co., catalog number 2724), 0.77 g water, 26 g ADN, and 139 g liquid ammonia. The content was hydrogenated at 70° C., under the total pressure of 1000 psig (7.00 MPa) at 1000 rpm. Total conversion of ADN was reached within 40 minutes on stream. The maximum yield of aminocapronitrile was 58% at 90% ADN conversion for a selectivity of 64%.

COMPARATIVE EXAMPLE 3

To a 50 cc autoclave, was charged 1.2 g of a 5% rhodium on alumina catalyst (obtained from Engelhard), 3.2 g ADN, and 35 ml liquid ammonia. The content was hydrogenated at 80° C., under the total pressure of 1060 psig (7.41 MPa), at 1500 rpm. Total conversion of AND was reached within 30 minutes on stream. The maximum yield of aminocapronitrile was 3% at 96% ADN conversion, with the major product being hexamethylene diamine.

EXAMPLE 1

1.2 g of sponge Ni catalyst (Degussa BLM 112W) was charged into a 50 cc autoclave, together with 2.0 g of tetramethylammonium hydroxide pentahydrate. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.00 MPa). After 24 minutes, the yield of 6-aminocapronitrile reached ca. 79% at 97% ADN conversion for a selectivity of 81%.

EXAMPLE 2

1.2 g of sponge Ni catalyst (Degussa BLM 112W) was charged into a 50 cc autoclave, together with 2.0 g of tetraethylammonium hydroxide as a 35 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.00 MPa). After 35 minutes the yield of 6-aminocapronitrile reached ca. 80% at 96% ADN conversion for a selectivity of 83%.

EXAMPLE 3

1.2 g of sponge Ni catalyst (Degussa ELM 112W) was charged into a 50 cc autoclave, together with 2.0 g of tetrapropylammonium hydroxide as a 1.0M solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1060 psig (7.41 MPa). After 25 minutes, the yield of 6-aminocapronitrile reached ca. 80% at 95% ADN conversion for a selectivity of 84%.

EXAMPLE 4

1.2 g of sponge Ni catalyst (Degussa ELM 112W) was charged into a 50 cc autoclave, together with 2.0 g of tetrabutylammonium hydroxide as a 40 wt % solution in water. Subsequently, 35 ml of liquid ammonia was added, and the mixture was heated to 70° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 70° C., and reacted with hydrogen at a total pressure of 1062 psig (7.43 MPa). After 30 minutes the yield of 6-aminocapronitrile reached ca. 80% at 94% ADN conversion for a selectivity of 85%.

EXAMPLE 5

1.2 g of a 5% rhodium on alumina catalyst (obtained from Engelhard) was charged into a 50 cc autoclave, together with 2.0 g of tetrabutylammonium hydroxide as a 40 wt % solution in water. Subsequently 35 cc of liquid ammonia was added, and the mixture was heated to 80° C. with stirring. The pressure was adjusted to 1000 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 75 minutes the yield of 6-aminocapronitrile reached 82% at 98% ADN conversion for a selectivity of 84%.

EXAMPLE 6

5.0 g of Raney® Co was charged into a 50 cc autoclave, together with 2.0 g of tetrabutylammonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hour. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 30 minutes the yield of 6-aminocapronitrile reached 71% at 94% ADN conversion for a selectivity of 76%.

EXAMPLE 7

0.3 g of sponge Ni catalyst (Degussa BLM 112W) was charged into a 50 cc autoclave, together with 0.5 g of tetrabutylammonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 40 minutes the yield of 6-aminocapronitrile reached ca. 73% at 92% ADN conversion for a selectivity of 79%.

EXAMPLE 8

A 50 cc autoclave was charged with 3.2 g of ADN, 1.2 g of sponge Ni catalyst (Degussa BLM 112W) and 0.5 g of tetrabutylphosphonium hydroxide as a 40 wt % solution in water. Subsequently, 35 ml of liquid ammonia was added, the mixture was heated to 80° C., and reacted with hydrogen at a total pressure of 1051 psig (7.35 MPa). After 6 minutes the yield of 6-aminocapronitrile reached ca. 72% at 90% ADN conversion for a selectivity of 80%.

EXAMPLE 9

1.2 g of sponge Ni catalyst (Degussa BLM 112W) was charged into a 50 cc autoclave, together with 2.0 g of tetrabutylphosphonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1055 psig (7.38 MPa). After 10 minutes the yield of 6-aminocapronitrile reached ca. 74% at 92% ADN conversion for a selectivity of 80%.

The results of the above examples are summarized in the following table:

| EX | Catalyst | Additive (Temp. ° C.) | Time | Yield | Conv. | Selec. |
|----|----------|----------------------|------|-------|-------|--------|
| C1 | Sponge Ni | None (60) | 30 m | 57% | 90% | 63% |
| C2 | Raney ® Co | None (70) | 40 m | 58% | 90% | 64% |
| C3 | Rh/Al$_2$O$_3$ | None (80) | 30 m | 3% | 96% | — |
| 1 | Sponge Ni | TMAOHP (80) | 24 m | 79% | 97% | 81% |
| 2 | Sponge Ni | TEAOH (80) | 35 m | 80% | 96% | 83% |
| 3 | Sponge Ni | TPAOH (80) | 25 m | 80% | 95% | 84% |
| 4 | Sponge Ni | TBAOH (70) | 30 m | 80% | 94% | 85% |
| 5 | Rh/Al$_2$O$_3$ | TBAOH (80) | 75 m | 82% | 98% | 84% |
| 6 | Raney ® Co | TBAOH (80) | 30 m | 71% | 94% | 76% |
| 7 | Sponge Ni | TBAOH (80) | 40 m | 73% | 92% | 79% |
| 8 | Sponge Ni | TBPOH (80) | 6 m | 72% | 90% | 80% |
| 9 | Sponge Ni | TBPOH (80) | 10 m | 74% | 92% | 80% |

TMAOHP tetramethylammonium hydroxide pentahydrate
TEAOH tetraethylammonium hydroxide
TPAOH tetrapropylammonium hydroxide
TBAOH tetrabutylammonium hydroxide
TBPOH tetrabutylphosphonium hydroxide

We claim:

1. A catalyst composition comprising (1) a hydrogenation catalyst suitable for hydrogenating a dinitrile to an aminonitrile; pretreated with (2) an additive comprising a compound selected from the group consisting of a tetraalkylammonium hydroxide compound and a tetraalkylphosphonium hydroxide compound.

2. The catalyst composition of claim 1, wherein the hydrogenation catalyst comprises a transition metal selected from the group consisting of iron, cobalt, nickel, rhodium and combinations thereof.

3. The catalyst composition of claim 1, wherein the catalyst further comprises one or more promoters selected from the group consisting of Group VIB and Group VII metals.

4. The catalyst composition of claim 1, wherein the hydroaenation catalyst is in sponge metal form.

5. The catalyst composition of claim 1, wherein the catalytic metal is supported on an inorganic support.

6. The catalyst composition of claim 1, wherein the alkyl groups of the tetraalkylammonium and tetraalkylphosphonium hydroxide compounds each individually contain from 1 to 8 carbon atoms.

7. The catalyst composition of claim 1, wherein the additive comprises a compound is selected from the group consisting of tetramethylammonium hydroxide, tetraethylammonium hydroxide, tetrapropylammonium hydroxide, tetrabutylammonium hydroxide and tetrabutylphosphonium hydroxide.

8. The catalyst composition of claim 1, wherein the weight ratio of additive to hydrogenation catalyst is in the range of from about 0.001:1 to about 2:1.

9. The catalyst composition of claim 1, wherein the hydrogenation catalyst comprises a transition metal selected from the group consisting of iron, cobalt, nickel, rhodium and combinations thereof; the additive comprises a compound is selected from the group consisting of tetramethylammonium hydroxide, tetraethylammonium hydroxide, tetrapropylammonium hydroxide, tetrabutylammonium hydroxide and tetrabutylphosphonium hydroxide; and the weight ratio of additive to hydrogenation catalyst is in the range of from about 0.001:1 to about 2:1.

10. A catalyst composition comprising a combination of (1) a hydrogenation catalyst suitable for hydrogenating a dinitrile to an aminonitrile; and (2) an additive comprising a tetraalkylphosphonium hydroxide compound.

11. The catalyst composition of claim 10, wherein the hydrogenation catalyst is pretreated with the additive.

12. The catalyst composition of claim 11, wherein the hydrogenation catalyst comprises a transition metal selected from the group consisting of iron, cobalt, nickel, rhodium and combinations thereof; and the weight ratio of additive to hydrogenation catalyst is in the range of from about 0.001:1 to about 2:1.

13. The catalyst composition of claim 10, wherein the hydrogenation catalyst comprises a transition metal selected from the group consisting of iron, cobalt, nickel, rhodium and combinations thereof.

14. The catalyst composition of claim 10, wherein the catalyst further comprises one or more promoters selected from the group consisting of Group VIB and Group VII metals.

15. The catalyst composition of claim 10, wherein the hydrogenation catalyst is in sponge metal form.

16. The catalyst composition of claim 10, wherein the catalytic metal is supported on an inorganic support.

17. The catalyst composition of claim 10, wherein the alkyl groups of the tetraalkylphosphonium hydroxide compounds each individually contain from 1 to 8 carbon atoms.

18. The catalyst composition of claim 10, wherein the additive comprises tetrabutylphosphonium hydroxide.

19. The catalyst composition of claim 10, wherein the weight ratio of additive to hydrogenation catalyst is in the range of from about 0.001:1 to about 2:1.

20. The catalyst composition of claim 10, wherein the hydrogenation catalyst comprises a transition metal selected from the group consisting of iron, cobalt, nickel, rhodium and combinations thereof; the additive comprises tetrabutylphosphonium hydroxide; and the weight ratio of additive to hydrogenation catalyst is in the range of from about 0.001:1 to about 2:1.

* * * * *

UNITED STATES PATENT AND TRADEMARK OFFICE
CERTIFICATE OF CORRECTION

PATENT NO. : 6,566,297 B2  Page 1 of 1
DATED : May 20, 2003
INVENTOR(S) : Ionkin Alex Sergey It is certified that error appears in the above-identified patent and that said Letters Patent is hereby corrected as shown below:

<u>Column 9,</u>
Line 37, "hydroaenation" should be -- hydrogenation --

Signed and Sealed this

Eighteenth Day of November, 2003

JAMES E. ROGAN
*Director of the United States Patent and Trademark Office*